United States Patent

Ghahremani et al.

(10) Patent No.: US 10,492,738 B2
(45) Date of Patent: Dec. 3, 2019

(54) MOTION DETECTION FOR NUCLEAR MEDICINE IMAGING

(71) Applicant: Siemens Medical Solutions USA, Inc., Malvern, PA (US)

(72) Inventors: Ahmadreza Ghahremani, Knoxville, TN (US); James Mark Long, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 142 days.

(21) Appl. No.: 15/885,916

(22) Filed: Feb. 1, 2018

(65) Prior Publication Data

US 2019/0231282 A1  Aug. 1, 2019

(51) Int. Cl.
| | |
|---|---|
| A61B 6/03 | (2006.01) |
| A61B 5/113 | (2006.01) |
| A61B 5/055 | (2006.01) |
| A61B 5/00 | (2006.01) |
| G01T 1/164 | (2006.01) |
| A61B 6/00 | (2006.01) |

(52) U.S. Cl.
CPC ........... *A61B 6/037* (2013.01); *A61B 5/0555* (2013.01); *A61B 5/113* (2013.01); *A61B 5/6892* (2013.01); *A61B 6/541* (2013.01); *G01T 1/1641* (2013.01)

(58) Field of Classification Search
CPC ....... A61B 6/037; A61B 5/6892; A61B 5/113; A61B 5/0555; A61B 6/541; G01T 1/1641
USPC ......................................................... 382/128
See application file for complete search history.

(56) References Cited

U.S. PATENT DOCUMENTS

| | | | |
|---|---|---|---|
| 7,365,334 B1 | 4/2008 | Gordon | |
| 7,630,528 B2 | 12/2009 | Kohler et al. | |
| 7,630,751 B2 | 12/2009 | Boese et al. | |
| 7,787,935 B2 | 8/2010 | Dumoulin et al. | |
| 7,993,275 B2 * | 8/2011 | Banet ................. | A61B 5/02255 600/485 |
| 9,002,079 B2 | 4/2015 | Sachs et al. | |
| 9,305,377 B2 | 4/2016 | Oliver et al. | |
| 2004/0147839 A1 * | 7/2004 | Moctezuma de la Barrera ......... | A61B 34/20 600/429 |
| 2007/0280508 A1 | 12/2007 | Ernst et al. | |
| 2010/0202664 A1 | 8/2010 | Busch et al. | |
| 2012/0033868 A1 | 2/2012 | Ren et al. | |
| 2012/0140054 A1 * | 6/2012 | Chen ..................... | H04N 7/18 348/77 |
| 2012/0278055 A1 | 11/2012 | Schweizer et al. | |
| 2013/0104906 A1 * | 5/2013 | Richards .............. | A61H 9/0078 128/845 |
| 2016/0256100 A1 * | 9/2016 | Jacofsky .............. | A47C 31/123 |
| 2017/0303864 A1 * | 10/2017 | Su ........................ | A61B 5/742 |
| 2018/0055174 A1 * | 3/2018 | Yim ..................... | A45C 13/185 |
| 2018/0214066 A1 * | 8/2018 | Goodall ................ | A41D 1/002 |
| 2018/0221216 A1 * | 8/2018 | Benz .................... | A61F 13/42 |

(Continued)

*Primary Examiner* — Jerome Grant, II (57) ABSTRACT

A patient bed for a medical treatment system is equipped with a plurality of flexible photodetector pads arranged on top surface of the patient bed, where the flexible photodetector pads generate an electrical signal from ambient lighting. A monitoring circuit monitors the electrical signal generated by the plurality of flexible photodetector pads while a patient on the patient bed, where any change in the voltage level of the electrical signal from the plurality of flexible photodetector pads represents a movement of the patient.

16 Claims, 6 Drawing Sheets

(56) References Cited

U.S. PATENT DOCUMENTS

2019/0133215 A1\* 5/2019 Whalen .............. A63B 24/0087
2019/0175076 A1\* 6/2019 Lustig ...................... A47C 7/72

\* cited by examiner

MOTION DETECTION FOR NUCLEAR MEDICINE IMAGING

FIELD

The present disclosure relates in general to detecting patient-motion during medical treatment.

BACKGROUND

In nuclear medicine imaging modalities (particularly in hybrid scanners) such as combination of single photon emission computed tomography and computed tomography (SPECT/CT), combination of positron emission tomography and computed tomography (PET/CT), combination of positron emission tomography and magnetic resonance imaging (PET/MRI)-performing a series of image acquisitions can take a considerable amount of time. In hybrid version of scanners, since one scanner needs to use image data captured previously from the other scanner (to calculate some parameters for updating reconstruction useful for attenuation map), precise matching between both scanners is crucial. In this example, an image may be generated by data that is acquired over a time period of up to 15 minutes or more. Because the final image is reconstructed from combination of portions of information obtained over time, any movement by a patient may result in blurring or other artifacts that reduce image quality or usability. Also for special medical treatment like radiotherapy, tracking the position of patient for a certain region during scan or treatment is important. However, it is frequently difficult for patients to remain still during the entire image acquisition process or portions thereof. For example, one form of motion frequently encountered in image acquisition is caused by breathing. For a certain imaging (or imaging portions) taking over 45 seconds, it may be difficult for patients to hold their breath that long. Similarly, patients may shift their weight or move in other fashions during image acquisition. Such movement of a patient relative to a detector or detectors results in inconsistencies between sets of data obtained over time relative to each other, and results in blurring or other artifacts. Presently known attempts to prevent or minimize patient movement are either uncomfortable or fail to adequately manage the patient movement. Presently known methods of tracking and monitoring the patient movement generally require complex hardware and software algorithms and fail to provide patient motion information in a timely and efficient manner.

SUMMARY

According to an aspect of the present disclosure, a patient bed for a medical treatment system that is configured for detecting patient movement is disclosed. The patent bed comprises: a plurality of flexible photodetector pads arranged on top surface of the patient bed, wherein the flexible photodetector pads generate a voltage signal from ambient lighting; and a monitoring circuit for monitoring the voltage signal generated by the plurality of flexible photodetector pads while a patient is lying on the patient bed, wherein any change in the voltage signal from the plurality of flexible photodetector pads represents motion of the patient.

A medical treatment system is also disclosed where the medical treatment system comprises: a patient bed; a plurality of flexible photodetector pads arranged on top surface of the patient bed, wherein the flexible photodetector pads generate a voltage signal from ambient lighting; and a monitoring circuit for monitoring the voltage signal generated by the plurality of flexible photodetector pads while a patient is lying on the patient bed during a medical treatment session; wherein any change in the voltage signal from the plurality of flexible photodetector pads represents movement by the patient and the medical treatment system is configured to screen the medical treatment data acquired during the period of the patient movement.

BRIEF DESCRIPTION OF THE DRAWINGS

The following will be apparent from elements of the figures, which are provided for illustrative purposes. The figures are schematic and are not necessarily to scale.

DETAILED DESCRIPTION

This description of the exemplary embodiments is intended to be read in connection with the accompanying drawings, which are to be considered part of the entire written description.

Figure 1:
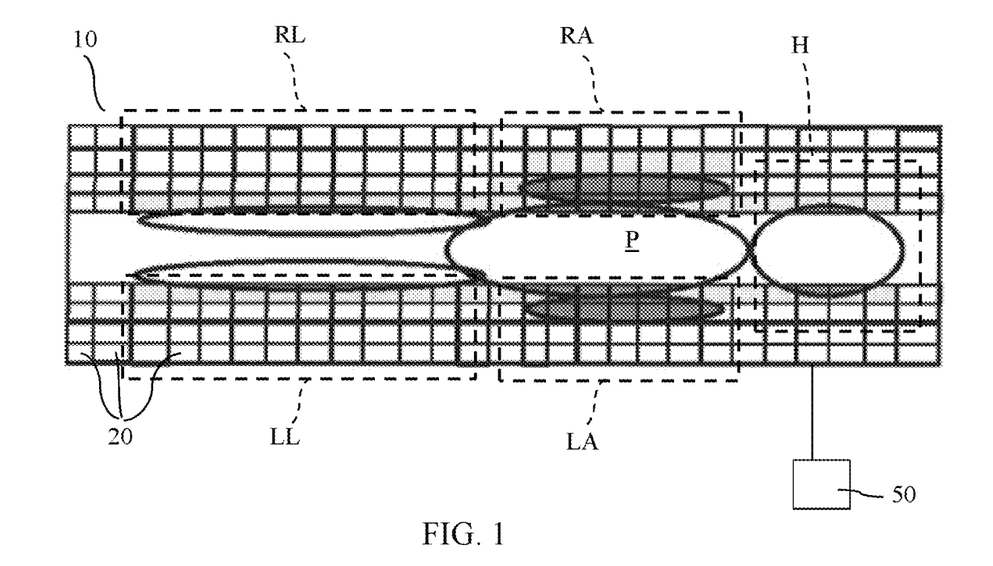
FIG. 1 is a schematic illustration of a patient bed configured for detecting the patient's body movement according to the present disclosure.

Referring to FIG. 1, a patient bed 10 for a medical treatment system is disclosed where the patient bed is configured with a plurality of flexible photodetector pads 20 for detecting body movement by the patient P during a treatment session. As used herein, the medical treatment system broadly refers to any system used for conducting a medical imaging or scanning session on a portion or portions of the patient body as well as any system that is used for performing a medical treatment procedure on a patient. Some non-limiting examples of such medical treatment system are combination of a single-photon emission computed tomography (SPECT) system, a positron emission tomography (PET) system, a computed tomography (CT) system, a magnetic resonance (MR) imaging system, or an external beam radiotherapy system. The patient bed disclosed herein can readily be incorporated into other similar types of medical treatment system where the patient needs to remain still during the treatment session and being able to detect even a subtle movement by the patient would be useful.

The plurality of flexible photodetector pads 20 are provided on the top surface of the patient bed 10 on which a patient lies down during the treatment session. Each of the flexible photodetector pads 20, as photodetectors, generates an electrical signal when exposed to light. As applied to the patient bed 10, there is sufficient ambient light around the patient bed 10 for the flexible photodetector pads 20 to produce electrical signal by being exposed to the ambient light.

Because the patient's body is placed on the top surface of the patient bed 10 over the plurality of flexible photodetector pads 20, some of the photodetector pads 20 will receive less ambient light than others because of the obstruction by the patient body P. Even if the patient body P is not casting a sharp shadow on the photodetector pads, the photodetector pads in close proximity of the patient body P will generally receive less ambient light because of the amount of light reaching those photodetector pads are less than for those photodetector pads farther away from the patient body because the patient body is obstructing the ambient light. This means that the level (i.e. the voltage) of electrical signal generated by the flexible photodetector pads 20 will vary depending on their location on the patient bed 10 with respect to the patient body P.

Regardless, as long as the patient remains still and does not move, the amount of light reaching each of the flexible photodetector pads 20 will remain constant and, in turn, the voltage level of the electrical signal generated by a given flexible photodetector pad will remain constant. However, if the patient moves, the patient body's shadow will move and the outline of the patient body's shadow will move or change and, in turn, will change the amount of light reaching those flexible photodetector pads, especially those in the vicinity of the shadow's outline. For the flexible photodetector pads that are directly along the shadow's outline, the amount of direct light coming from the light. Additionally, the movement of the patient body P also changes the amount of ambient light affect the amount of The initial level of the electrical signal generated by the photodetector pads can be established as the baseline and by monitoring the electrical signals from the flexible photodetector pads one can detect a movement by the patient P. That is because any movement in the patient body P will result in a change in the voltage level of the electrical signal from those flexible photodetector pads that are near or under the part of the patient body P that moved because even a small body movement will change the amount of light reaching some of the flexible photodetector pads that are near or under the part of the patient body P.

A monitoring circuit 50 configured to receive and record the electrical signal generated by each of the plurality of flexible photodetector pads is provided for monitoring the voltage level of the electrical signal generated by the flexible photodetector pads. Any change in the voltage level of the electrical signal from one or more of the plurality of flexible photodetector pads represents a movement of the patient body P. By mapping the location of each of the flexible photodetector pads on the patient bed 10, one can correlate the change detected in the electrical signal output from any given flexible photodetector pad to a region of the patient body that moved.

In situations where there are no ambient light or insufficient ambient light, one or more additional light sources 70 can be provided to supplement the ambient light. For example, in one embodiment, the additional light sources can be placed above the patient and illuminate the patient P and the patient bed 10.

In some embodiments, the monitoring circuit 50 is configured to monitor the voltage signal generated by each of the plurality of flexible photodetector pads individually.

In some embodiments, the plurality of flexible photodetector pads 20 is defined into one or more groups where each group monitors a different region of the patient body P. Each group comprises a group of flexible photodetector pads that are in proximity to a particular region of the patient body P. Therefore, each group represents a different region of the patent body P and depending on the region of the body that is being scanned or treated by the medical treatment system, only a particular group of flexible photodetector pads can be monitored to detect any movement in the region of the patient body that is of interest.

For example, in FIG. 1, the group of flexible photodetector pads near the patient's head is identified as group H. The group H can be used to monitor any head movement. The group of flexible photodetector pads near the patient's right arm is identified as group RA. The group of flexible photodetector pads near the patient's left arm is identified as group LA. The group of flexible photodetector pads near the patient's right leg is identified as group RL. The group of flexible photodetector pads near the patient's left leg is identified as group LL. These are just examples and the particular grouping in a given medical treatment system can be different depending on the needs of that system.

In some embodiments, the monitoring circuit 50 is configured to monitor the electrical signal generated by each of the plurality of flexible photodetector pads individually, and any change in the voltage level of the electrical signal from one or more of the plurality of flexible photodetector pads in a group represents a movement of the patient's body region corresponding to said group. In some embodiments, the monitoring circuit 50 is configured to monitor the electrical signal generated by each of the one or more groups individually, and any change in the voltage level of the electrical signal of a group represents a movement of the patient's body region corresponding to said group.

In some embodiments, not all of the groups need to be electrically connected to the monitoring circuit 50 the same way. For example, some of the groups can be configured to generate one electrical signal output to be monitored for each group while some of the other groups can be configured to generate separate electrical signal output for each individual flexible photodetector pad to be monitored.

In some embodiments, each of the flexible photodetector pads in a given group can be electrically connected in series and connected to the monitoring circuit 50 so that the given group generates one electrical signal output to be monitored. For example, in this embodiment, the group H would generate one electrical signal output representing the patient's head. A change in the voltage of the electrical signal output from the group H would indicate a head movement.

In some embodiments, each of the flexible photodetector pads 20 in a given group can be individually electrically connected to the monitoring circuit 50 independent of the other flexible photodetector pads in the group so that the electrical signal output from each pad is monitored individually. Thus, a change in any one of the flexible photodetector pad in that given group will provide an indication that the patient body region corresponding to that given group moved and additionally provide the granularity to pinpoint to the particular area within the body region that moved, if such granularity is desired.

Figure 2:
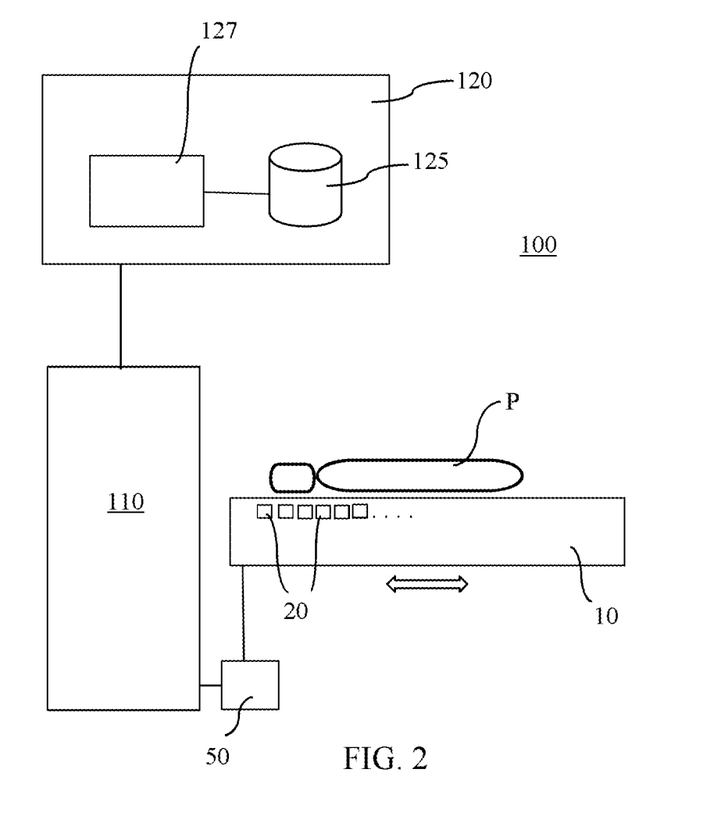
FIG. 2 is a schematic illustration of the medical treatment system according to the present disclosure.

Referring to FIG. 2, a medical treatment system 100 incorporating the patient bed 10 described above is also disclosed. The medical treatment system 100 can comprise a detector or treatment unit 110, a patient bed 10, a plurality of flexible photodetector pads 20 arranged on top surface of the patient bed, wherein the flexible photodetector pads generate an electrical signal from ambient lighting; and a monitoring circuit 50 for monitoring and recording the electrical signal generated by the plurality of flexible photodetector pads while a patient is placed on the patient bed during a medical treatment session. Any change in the voltage level of the electrical signal from the plurality of flexible photodetector pads represents movement by the patient and the medical treatment system is configured to screen the medical treatment data acquired during the period of the patient movement.

In some embodiments of the medical treatment system 100, the monitoring circuit 50 is configured to monitor the electrical signal generated by each of the plurality of flexible photodetector pads 20 individually.

The electrical signal monitoring data from the monitoring circuit 50 is processed by one or more computer processors 127 of a computer 120. The graphical depiction of the computer 120 in FIG. 2 is provided by way of illustration only, and computer 120 may include one or more separate computing devices. The flexible detector pad electrical signal data can be stored in a storage memory unit 125 of the computer 120. The computer 120 can include one or more processing electronics for processing the electrical signal received from the flexible photodetector pads.

In some embodiments of the medical treatment system 100, the plurality of flexible photodetector pads 20 are defined into one or more groups (H, RA, RL, LA, LL) as described above. Each group representing a region of the patient's body and each group generating an electrical signal. The monitoring circuit 50 is configured to monitor the electrical signal generated by each of the one or more groups individually. Any change in the electrical signal of one or more groups represent motion of patient's body regions that correspond to the one or more groups.

In some embodiments of the medical treatment system 100, the monitoring circuit 50 is configured to monitor the electrical signal generated by each of the plurality of flexible photodetector pads individually, and any change in the voltage level of the electrical signal from one or more of the plurality of flexible photodetector pads in a group represents a movement of the patient's body region corresponding to the group.

In some embodiments of the medical treatment system 100, the monitoring circuit 50 is configured to monitor the electrical signal generated by each of the one or more groups individually, and any change in the voltage level of the electrical signal of a group represents a movement of the patient's body region corresponding to the group.

In some embodiments, the medical treatment system 100 further comprises one or more additional light source 70 illuminating the patient bed 10 from above to enhance the voltage signal generated by the plurality of flexible photodetector pads 20.

In some embodiments of the medical treatment system 100, the medical treatment system is one of a single-photon emission computed tomography (SPECT), a positron emission tomography (PET), computed tomography (CT), a magnetic resonance (MR) imaging system, or an external beam radiotherapy.

Figure 3:
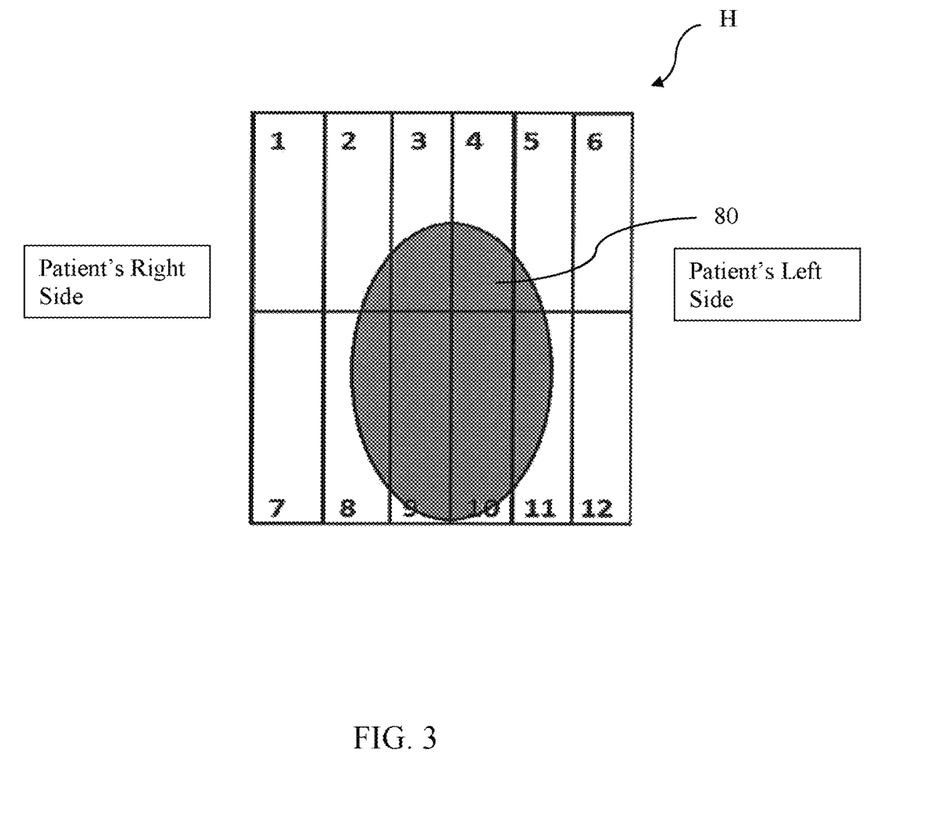
FIG. 3 is a schematic illustration of the outline of the patient's head that is positioned on top of the flexible photodetector pad group H.
Figure 4:
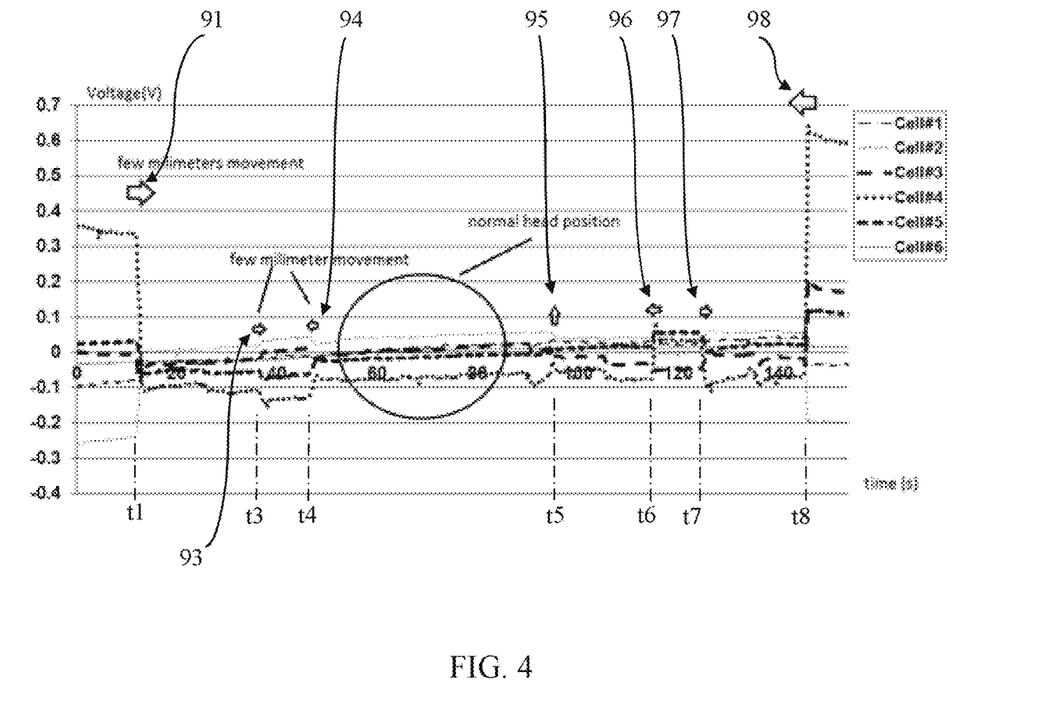
FIG. 4 is a voltage plot of the electrical signal output from the flexible photodetector pads 1 through 6 in the photodetector pad group H.
Figure 5:
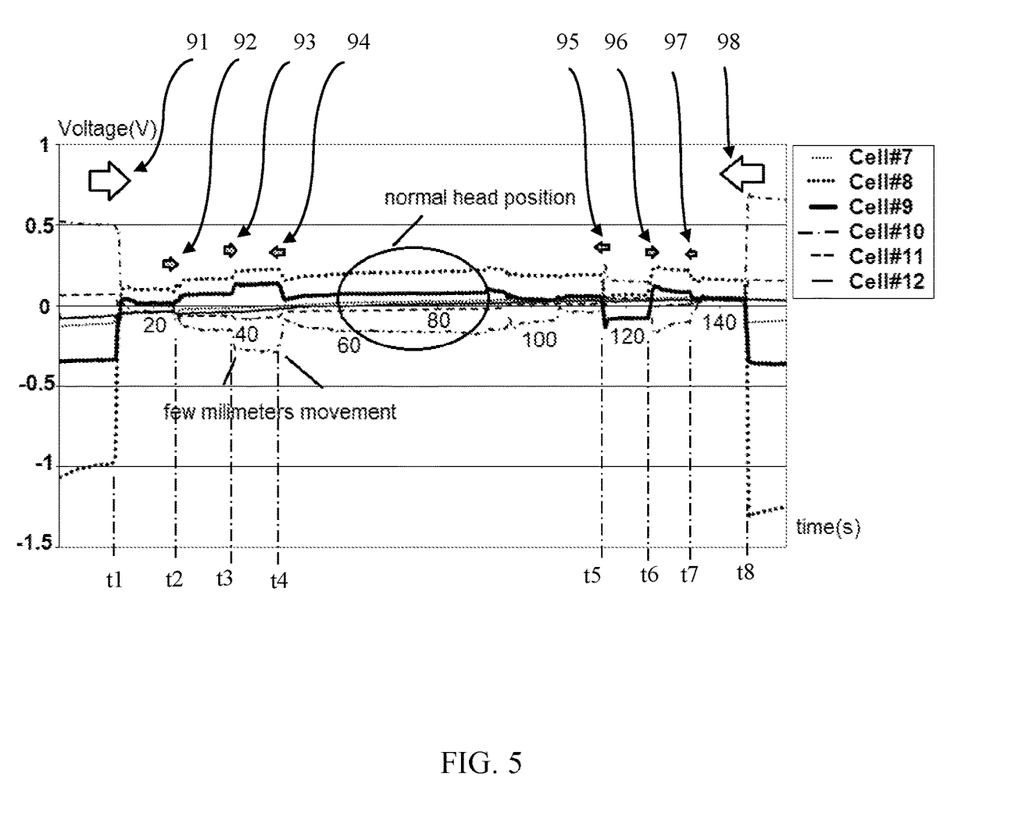
FIG. 5 is a voltage plot of the electrical signal output from the flexible photodetector pads 7 through 12 in the photodetector pad group H.

FIG. 3 shows a schematic illustration of the flexible photodetector pad group H with an outline of the patient's head 80 that is positioned on top of the photodetector pad group H. The photodetector pad group H in this example is formed by an array of flexible photodetector pads identified with numbers 1 through 12. FIG. 4 shows the voltage plot of the electrical signal output generated by the photodetector pads 1 through 6, labeled as cells #1 through #6 in the plot. FIG. 5. Shows the voltage plot of the electrical signal output generated by the photodetector pads 7 through 12, labeled as cells #7 through #12 in the plot.

The arrows 91, 92, 93, 94, 95, 96, 97, 98 in the plots of FIGS. 4 and 5 indicate the direction of the head movement that were detected at the corresponding time points t1, t2, t3, t4, t5, t6, t7, and t8, respectively. Simply by comparing the voltage level of the cells at the neighbor located in horizontal line or vertical line at a particular time (when voltage signal is changing), we are able to detect the direction of movement in three dimensions in space (right-left, up-down, or rising up from the bed).

For instance, in the plot shown in FIG. 4, at time point t3 voltage signals are changing for the cells #2, #3, #4, and #5 in the first row of detectors shown in FIG. 3. At time point t3, the voltage level for cell #2, and #3 jumps up (translated as more light, i.e. higher intensity light, impacting the surface of the photodetectors), and the voltage level for the cell #4 and #5 drops (translated as less light, i.e. lower intensity light, impacting the surface of the photodetectors). It means that the shadow of the head is moving horizontally toward the left side of the patient which is shown in FIG. 4 with arrow 93. Note the directions Left and Right from the patient P's perspective is identified in FIG. 3. The same movement can be detected at time point t3 from the second row of detectors (cells #8, #9, #10, and #11). The voltage level plot of the electrical signals from the cells #8, #9, #10, and #11 is shown in FIG. 5. It is consistent with the observation made with the first row of the detectors for the head region. The time interval between t3 and t4 exhibiting the substantially flat voltage plot indicates the normal head position, i.e. the head position that is required for the medical treatment procedure.

Figure 6:
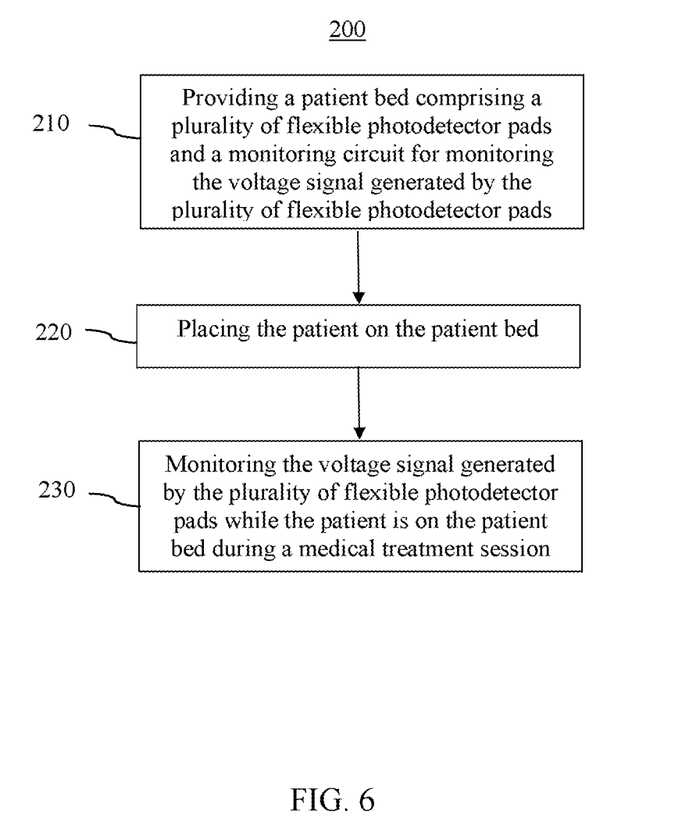
FIG. 6 shows a flowchart of a method for detecting a movement of a patient placed on a patient bed during a medical treatment session using a medical treatment system according to the present disclosure.

Referring to the flowchart 200 shown in FIG. 6, a method for detecting a movement of a patient P placed on the patient bed 10 during a medical treatment session using a medical treatment system is disclosed. The method includes providing the patient bed 10 as described above. (See box 210). Next, the method includes placing the patient P on the patient bed 10, (See box 220); and monitoring the electrical signal generated by the plurality of flexible photodetector pads 20 while the patient is on the patient bed during a medical treatment session. (See box 230).

In some embodiments, monitoring the electrical signal generated by the plurality of flexible photodetector pads comprises monitoring each of the plurality of flexible photodetector pads individually. In some embodiments, where the plurality of flexible photodetector pads are defined into one or more groups, each group representing a region of the patient's body, the method includes monitoring the electrical signal generated by each of the plurality of flexible photodetector pads individually. Any change in the voltage level of the electrical signal from one or more of the plurality of flexible photodetector pads in a group represents a movement of the patient's body region corresponding to that group.

In some embodiments, where the plurality of flexible photodetector pads are defined into one or more groups, each group representing a region of the patient's body and each group, the method includes monitoring the electrical signal generated by each of the one or more groups individually. Any change in the voltage level of the electrical signal from a group represents a movement of the patient's body region corresponding to that group.

The description of the various embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A patient bed for a medical treatment system comprising:
   a plurality of flexible photodetector pads arranged on a top surface of the patient bed, wherein the flexible photodetector pads generate an electrical signal from ambient lighting; and
   a monitoring circuit for monitoring the electrical signal generated by the plurality of flexible photodetector pads while a patient is placed on the patient bed, wherein any change in voltage level of the electrical signal from one or more of the plurality of flexible photodetector pads represents a movement by the patient,
   wherein the medical treatment system is one of a single-photon emission computed tomography (SPECT), a positron emission tomography (PET), computed tomography (CT), a magnetic resonance (MR) imaging system, an external beam radiotherapy, or hybrid version of scanners (SPECT/CT, PET/CT, or PET/MRI).

2. The patient bed of claim 1, wherein the monitoring circuit is configured to monitor the voltage signal generated by each of the plurality of flexible photodetector pads individually.

3. The patient bed of claim 1, wherein the plurality of flexible photodetector pads are defined into one or more groups, each group representing a region of the patient's body,
   wherein the monitoring circuit is configured to monitor the electrical signal generated by each of the plurality of flexible photodetector pads individually, and
   wherein any change in voltage level of the electrical signal from one or more of the plurality of flexible photodetector pads in a group represents a movement of the patient's body region corresponding to said group.

4. The patient bed of claim 1, wherein the plurality of flexible photodetector pads are defined into one or more groups, each group representing a region of the patient's body and each group generating an electrical signal,
   wherein the monitoring circuit is configured to monitor voltage level of the electrical signal generated by each of the one or more groups individually, and
   wherein any change in the voltage level of the electrical signal of a group represents a movement of the patient's body region corresponding to said group.

5. The patient bed of claim 1, wherein the plurality of flexible photodetector pads are defined into one or more groups, each group representing a region of the patient's body, wherein some of the groups are configured to generate one electrical signal to be monitored for each group while one or more of the other groups are configured to generate separate electrical signal for each individual flexible photodetector pad.

6. The patient bed of claim 1, further comprising one or more additional light source illuminating the patient bed from above to enhance the electrical signal generated by the plurality of flexible photodetector pads.

7. A medical treatment system comprising:
   a patient bed;
   a plurality of flexible photodetector pads arranged on top surface of the patient bed, wherein the flexible photodetector pads generate an electrical signal from ambient lighting; and
   a monitoring circuit for monitoring the electrical signal generated by the plurality of flexible photodetector pads while a patient is placed on the patient bed during a medical treatment session, wherein any change in voltage level of the electrical signal from one or more of the plurality of flexible photodetector pads represents a movement by the patient and the medical treatment system is configured to screen the medical treatment data acquired during the period of the patient movement,
   wherein the medical treatment system is one of a single-photon emission computed tomography (SPECT), a positron emission tomography (PET), computed tomography (CT), a magnetic resonance (MR) imaging system, or an external beam radiotherapy.

8. The medical treatment system of claim 7, wherein the monitoring circuit is configured to monitor the electrical signal generated by each of the plurality of flexible photodetector pads individually.

9. The medical treatment system of claim 7, wherein the plurality of flexible photodetector pads are defined into one or more groups, each group representing a region of the patient's body,
   wherein the monitoring circuit is configured to monitor voltage level of the electrical signal generated by each of the plurality of flexible photodetector pads individually, and
   wherein any change in the voltage level of the electrical signal from one or more of the plurality of flexible photodetector pads in a group represents a movement of the patient's body region corresponding to said group.

10. The medical treatment system of claim 7, wherein the plurality of flexible photodetector pads are defined into one or more groups, each group representing a region of the patient's body and each group generating an electrical signal,
    wherein the monitoring circuit is configured to monitor the electrical signal generated by each of the one or more groups individually, and
    wherein any change in voltage level of the electrical signal of a group represents a movement of the patient's body region corresponding to said group.

11. The medical treatment system of claim 7, wherein the plurality of flexible photodetector pads are defined into one or more groups, each group representing a region of the patient's body, wherein some of the groups are configured to generate one electrical signal to be monitored for each group while one or more of the other groups are configured to generate separate electrical signal for each individual flexible photodetector pad.

12. The medical treatment system of claim 7, further comprising one or more additional light source illuminating the patient bed from above to enhance the electrical signal generated by the plurality of flexible photodetector pads.

13. A method for detecting a movement of a patient placed on a patient bed during a medical treatment session using a medical treatment system, the method comprising:
    providing the patient bed comprising:
      a plurality of flexible photodetector pads arranged on top surface of the patient bed, wherein the flexible photodetector pads generate an electrical signal from ambient lighting; and a monitoring circuit for monitoring the electrical signal generated by the plurality of flexible photodetector pads while a patient is placed on the patient bed, wherein any change in voltage level of the electrical signal from one or more of the plurality of flexible photodetector pads represents a movement by the patient;

placing the patient on the patient bed; and monitoring the electrical signal generated by the plurality of flexible photodetector pads while the patient is on the patient bed during a medical treatment session, wherein the medical treatment system is one of a single-photon emission computed tomography (SPECT), a positron emission tomography (PET), computed tomography (CT), a magnetic resonance (MR) imaging system, an external beam radiotherapy, or hybrid version of scanners (SPECT/CT, PET/CT, or PET/MRI).

14. The method of claim 13, wherein the monitoring the electrical signal generated by the plurality of flexible photodetector pads comprises monitoring each of the plurality of flexible photodetector pads individually.

15. The method of claim 13, wherein the plurality of flexible photodetector pads are defined into one or more groups, each group representing a region of the patient's body; and monitoring the electrical signal generated by each of the plurality of flexible photodetector pads individually, wherein any change in voltage level of the electrical signal from one or more of the plurality of flexible photodetector pads in a group represents a movement of the patient's body region corresponding to said group.

16. The method of claim 13, wherein the plurality of flexible photodetector pads are defined into one or more groups, each group representing a region of the patient's body and each group generating an electrical signal; and monitoring the electrical signal generated by each of the one or more groups individually, wherein any change in voltage level of the electrical signal of a group represents a movement of the patient's body region corresponding to said group.

* * * * *